United States Patent
Sun

(10) Patent No.: US 10,611,833 B2
(45) Date of Patent: Apr. 7, 2020

(54) HUMANIZED ANTI-HUMAN EPIDERMAL GROWTH FACTOR RECEPTOR ANTIBODY AND APPLICATION THEREOF

(71) Applicant: WELSON PHARMACEUTICALS, INC., Beijing (CN)

(72) Inventor: Le Sun, Beijing (CN)

(73) Assignee: WELSON PHARMACEUTICALS, INC., Haidian District Beijing (CN)

( * ) Notice: Subject to any disclaimer, the term of this patent is extended or adjusted under 35 U.S.C. 154(b) by 272 days.

(21) Appl. No.: 15/124,288

(22) PCT Filed: Mar. 6, 2015

(86) PCT No.: PCT/CN2015/073801
§ 371 (c)(1),
(2) Date: Sep. 12, 2018

(87) PCT Pub. No.: WO2015/131855
PCT Pub. Date: Sep. 11, 2015

(65) Prior Publication Data
US 2019/0010227 A1    Jan. 10, 2019

(30) Foreign Application Priority Data
Mar. 7, 2014 (CN) .......................... 2014 1 0083224

(51) Int. Cl.
| | | |
|---|---|---|
| A61K 39/395 | (2006.01) | |
| C07K 16/28 | (2006.01) | |
| C12N 15/63 | (2006.01) | |
| A61P 35/00 | (2006.01) | |
| A61P 37/02 | (2006.01) | |
| C07K 16/22 | (2006.01) | |
| A61P 31/00 | (2006.01) | |

(52) U.S. Cl.
CPC .............. *C07K 16/28* (2013.01); *A61P 31/00* (2018.01); *A61P 35/00* (2018.01); *A61P 37/02* (2018.01); *C07K 16/22* (2013.01); *C07K 16/2863* (2013.01); *C12N 15/63* (2013.01); *C07K 2317/24* (2013.01); *C07K 2317/515* (2013.01); *C07K 2317/73* (2013.01); *C07K 2317/76* (2013.01); *C07K 2317/92* (2013.01)

(58) Field of Classification Search
None
See application file for complete search history.

(56) References Cited

U.S. PATENT DOCUMENTS 5,459,061 A * 10/1995 Sato ................... C07K 16/2863
435/334
5,530,101 A * 6/1996 Queen ................... C07K 16/00
424/133.1

FOREIGN PATENT DOCUMENTS

| CN | 101277716 A | 10/2008 |
|---|---|---|
| CN | 104059148 A | 9/2014 |

OTHER PUBLICATIONS

International Search Report for PCT/CN2015/073801, dated Jun. 12, 2015.

* cited by examiner

*Primary Examiner* — Meera Natarajan
(74) *Attorney, Agent, or Firm* — Brinks Gilson & Lione

(57) ABSTRACT

Disclosed herein are humanized anti-Epidermal Growth Factor (EGF) Receptor antibodies which can inhibit the proliferation of cells expressing the EGF receptor. Humanized anti-EGFR antibodies are capable of binding to the surface of cells and killing the EGF receptor overexpression cells. The invention presents the humanized anti-EGFR antibodies which bind to different epitope and inhibit the tumor formation in a different way than Erbitux. Most importantly, once bound to the surface EGFR, these new anti-EGFR antibodies will internalize rather quickly, which made them ideal candidate for antibody drug conjugation and other biotherapy. The invention also features method of humanization which leads to 90% of the amino acid sequences are human sequence, and significantly reduce the risk of human anti-mouse immunogenicity. The present invention also demonstrated that the humanized anti-EGFR antibodies have the affinity to EGFR in the range of 2.3 nM, which is very similar to the mouse anti-EGFR monoclonal antibody LA22.

20 Claims, 8 Drawing Sheets
Specification includes a Sequence Listing.

Fig. 8

```
h0-LA22 a.a.    MRLPAQLLGLLMLWVPGSSGDVVMTQSPLSLPVTLGQPAS    40
h1-LA22A a.a.   MRLPAQLLGLLMLWVPGSSGDVVMTQSPLSLPVTLGQ AS    40
h2-LA22 a.a.    MRLPAQLLGLLMLWVPGSSGDVVMTQSPLSLPVTLGQPAS    40
Consensus       mrlpaqllgllmlwvpgssgdvvmtqspslpvtlgq as h0-LA22 a.a.    ISCRSSQSLVHSNGNTYLHW QQRPGQSPRRLIYKVSNRF    80
h1-LA22A a.a.   ISCRSSQSLVHSNGNTYLHW QQRPGQSPR LIYKVSNRF    80
h2-LA22 a.a.    ISCRSSQSLVHSNGNTYLHW QQRPGQSPR LIYKVSNRF    80
Consensus       iscrssqslvhsngntylhw qqrpgqspr  liykvsnrf h0-LA22 a.a.    SGVPDRFSGSGSGTDFTLKISRVEAEDVG Y CSQSSHVP   120
h1-LA22A a.a.   SGVPDRFSGSGSGTDFTLKISRVEAEDVG Y CSQSSHVP   120
h2-LA22 a.a.    SGVPDRFSGSGSGTDFTLKISRVEAEDVG IY CSQSSHVP  120
Consensus       sgvpdrfsgsgsgtdftlkisrveaedvg y  csqsshvp h0-LA22 a.a.    PAFGGGTKLEIK              a.a.    a.a.     122
h1-LA22A a.a.   PAFGGGTKLEIK     a.a.     a.a.    a.a.     122
h2-LA22 a.a.    PAFGGGTKLEIK              a.a.    a.a.     122
Consensus       pafgggtkleik                      a.a.
```

Fig. 9

```
h0-LA22H1-AA.seq   MELGLSWVFLVAILEGVQCEVQLVESGGGLVQPGGSLRLS    40
h1-LA22H1-AA.seq   MELGLSWVFLVAILEGVQCEVQLVESGGGLVQPGGSLRLS    40
h2-LA22H1-AA.seq   MELGLSWVFLVAILEGVQCEVQLVESGGGLVQPGGSLRLS    40
h3-LA22H1-AA.seq   MELGLSWVFLVAILEGVQCEVQLVESGGGLVQPGGSLRLS    40
h4-LA22H1-AA.seq   MELGLSWVFLVAILEGVQCEVQLVESGGGLVQPGGSLRLS    40
Consensus          melglswvflvailegvqcevqlvesggglvqpggslrls h0-LA22H1-AA.seq   CAAS EYEFPSHDMSWVRQ APGK LEWVSAITSDGISTYYP   80
h1-LA22H1-AA.seq   CE   EYEFPSHDMSWVRQ APGK LEWVSAITSDGISTYYP   80
h2-LA22H1-AA.seq   CE   EYEFPSHDMSWVRQ APGK LEWVSAITSDGISTYYP   80
h3-LA22H1-AA.seq   CA   EYEFPSHDMSWVRQ TPGK LEWVSAITSDGISTYYP   80
h4-LA22H1-AA.seq   CA   EYEFPSHDMSWVRQ TPGK RLEWVSAITSDGISTYYP  80
Consensus          c    eyefpshdmswvrq  pgk  lewvsaitsdgistyyp h0-LA22H1-AA.seq   DTMERRFTISRDN K TLYLQM SLRAEDTAVYYCARHDW   120
h1-LA22H1-AA.seq   DTMERRFTISRDN K TLYLQM SLRAEDTAVYYCARHDW   120
h2-LA22H1-AA.seq   DTMERRFTISRDN TKK TLYLQM SLRAEDTAVYYCARHDW 120
h3-LA22H1-AA.seq   DTMERRFTISRDN K TLYLQM SLRAEDTAVYYCARHDW   120
h4-LA22H1-AA.seq   DTMERRFTISRDN K TLYLQM SLRAEDTAVYYCARHDW   120
Consensus          dtmerrftisrdn k  tlylqm  slraedtavyycarhdw h0-LA22H1-AA.seq   DEGFASWGQGTLVTVSSASTKGPSVFPLAPSSKSTSGGTA   160
h1-LA22H1-AA.seq   DEGFASWGQGTLVTVSSASTKGPSVFPLAPSSKSTSGGTA   160
h2-LA22H1-AA.seq   DEGFASWGQGTLVTVSSASTKGPSVFPLAPSSKSTSGGTA   160
h3-LA22H1-AA.seq   DEGFASWGQGTLVTVSSASTKGPSVFPLAPSSKSTSGGTA   160
h4-LA22H1-AA.seq   DEGFASWGQGTLVTVSSASTKGPSVFPLAPSSKSTSGGTA   160
Consensus          degfaswgqgtlvtvssastkgpsvfplapssкstsggta h0-LA22H1-AA.seq   ALGCLVKDYFP                               171
h1-LA22H1-AA.seq   ALGCLVKDYFP                               171
h2-LA22H1-AA.seq   ALGCLVKDYFP                               171
h3-LA22H1-AA.seq   ALGCLVKDYFP                               171
h4-LA22H1-AA.seq   ALGCLVKDYFP                               171
Consensus          algclvkdyfp
```

Fig. 10

SEQUENCE LISTING

```
<160> NUMBER OF SEQ ID NOS: 26

<210> SEQ ID NO 1
<211> LENGTH: 118
<212> TYPE: PRT
<213> ORGANISM: Artificial Sequence
<220> FEATURE:
<223> OTHER INFORMATION: mLA22 heavy chain variable region

<400> SEQUENCE: 1

Glu Val Gln Leu Val Glu Ser Gly Gly Gly Leu Val Gln Pro Gly Glu
1               5                   10                  15

Ser Leu Lys Leu Ser Cys Glu Ser Asn Glu Tyr Glu Phe Pro Ser His
            20                  25                  30

Asp Met Ser Trp Val Arg Lys Thr Pro Glu Glu Arg Leu Glu Leu Val
        35                  40                  45

Ala Ala Ile Thr Ser Asp Gly Ile Ser Thr Tyr Tyr Pro Asp Thr Met
    50                  55                  60

Glu Arg Arg Phe Leu Ile Ser Arg Asp Asn Thr Lys Lys Thr Leu Tyr
65                  70                  75                  80

Leu Gln Met Ser Ser Leu Arg Ser Glu Asp Thr Ala Leu Tyr Tyr Cys
                85                  90                  95

Ser Arg His Asp Trp Asp Glu Gly Phe Ala Ser Trp Gly Gln Gly Thr
            100                 105                 110

Leu Val Thr Val Ser Ala
        115

<210> SEQ ID NO 2
<211> LENGTH: 112
<212> TYPE: PRT
<213> ORGANISM: Artificial Sequence
<220> FEATURE:
<223> OTHER INFORMATION: mLA22 light chain variable region

<400> SEQUENCE: 2

Asp Val Val Met Thr Gln Thr Pro Leu Ser Leu Pro Val Ser Leu Gly
1               5                   10                  15
```

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Ile Tyr Phe Cys Ser Gln Ser
                85                  90                  95

Ser His Val Pro Pro Ala Phe Gly Gly Gly Thr Lys Leu Glu Ile Lys
            100                 105                 110

<210> SEQ ID NO 3
<211> LENGTH: 354
<212> TYPE: DNA
<213> ORGANISM: Artificial Sequence
<220> FEATURE:
<223> OTHER INFORMATION: mLA22 heavy chain variable region

<400> SEQUENCE: 3
gaggtgcaac tggtggagtc tgggggaggc ttagtgcagc ctggagagtc cctgaaactc      60
tcctgtgaat ccaatgaata cgaattccct tcccatgaca tgtcttgggt ccgcaagact     120
ccggaggaga ggctggagtt ggtcgcagcc attactagtg atggtattag cacctactat     180
ccagacacca tggagagacg attcctcatc tccagagaca taccaagaa gaccctgtac      240 ctgcaaatga gcagtctgag gtctgaggac acagccttgt attactgttc aagacatgac     300
tgggacgagg ggtttgcttc ctggggccaa gggactctgg tcactgtctc tgca           354

<210> SEQ ID NO 4
<211> LENGTH: 336
<212> TYPE: DNA
<213> ORGANISM: Artificial Sequence
<220> FEATURE:
<223> OTHER INFORMATION: mLA22 light chain variable region

<400> SEQUENCE: 4
gatgttgtga tgacccaaac tccactctcc ctgcctgtca gtcttggaga tcaagcctcc      60
atctcttgca gatctagtca gagccttgta cacagtaatg aaacaccta tttacattgg     120 tatctgcaga agccaggcca gtctccaaag ctcctgatct acaaagtttc caaccgattt     180
tctggggtcc cagacaggtt cagtggcagt ggatcaggca cagatttcac actcaagatc     240
agcagagtgg aggctgagga tctgggaatt tatttctgct ctcaaagttc acatgttcct     300
ccggcgttcg gtggagggac caagctggag atcaaa                               336

<210> SEQ ID NO 5
<211> LENGTH: 171
<212> TYPE: PRT
<213> ORGANISM: Artificial Sequence
<220> FEATURE:
<223> OTHER INFORMATION: Chimeric heavy chain variable region

<400> SEQUENCE: 5

Met Asp Phe Gly Leu Ser Leu Val Phe Leu Val Leu Ile Leu Lys Ser
1               5                   10                  15

Val Gln Cys Glu Val Gln Leu Val Glu Ser Gly Gly Gly Leu Val Gln
            20                  25                  30

Pro Gly Glu Ser Leu Lys Leu Ser Cys Glu Ser Asn Glu Tyr Glu Phe

```
                35                  40                  45

Pro Ser His Asp Met Ser Trp Val Arg Lys Thr Pro Glu Glu Arg Leu
50                  55                  60

Glu Leu Val Ala Ala Ile Thr Ser Asp Gly Ile Ser Thr Tyr Tyr Pro
65                  70                  75                  80

Asp Thr Met Glu Arg Arg Phe Leu Ile Ser Arg Asp Asn Thr Lys Lys
                85                  90                  95

Thr Leu Tyr Leu Gln Met Ser Ser Leu Arg Ser Glu Asp Thr Ala Leu
            100                 105                 110

Tyr Tyr Cys Ser Arg His Asp Trp Asp Glu Gly Phe Ala Ser Trp Gly
        115                 120                 125

Gln Gly Thr Leu Val Thr Val Ser Ala Ala Ser Thr Lys Gly Pro Ser
130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro
            165                 170
```

<210> SEQ ID NO 6
<211> LENGTH: 131
<212> TYPE: PRT
<213> ORGANISM: Artificial Sequence
<220> FEATURE:
<223> OTHER INFORMATION: Chimeric light chain variable region

<400> SEQUENCE: 6

```
Met Lys Leu Pro Val Arg Leu Leu Val Leu Met Phe Trp Ile Pro Ala
1               5                   10                  15

Ser Ser Ser Asp Val Val Met Thr Gln Thr Pro Leu Ser Leu Pro Val
                20                  25                  30

Ser Leu Gly Asp Gln Ala Ser Ile Ser Cys Arg Ser Ser Gln Ser Leu
            35                  40                  45

Val His Ser Asn Gly Asn Thr Tyr Leu His Trp Tyr Leu Gln Lys Pro
        50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Ile Tyr Phe Cys
            100                 105                 110

Ser Gln Ser Ser His Val Pro Pro Ala Phe Gly Gly Gly Thr Lys Leu
        115                 120                 125

Glu Ile Lys
    130
```

<210> SEQ ID NO 7
<211> LENGTH: 171
<212> TYPE: PRT
<213> ORGANISM: Artificial Sequence
<220> FEATURE:
<223> OTHER INFORMATION: H0-LA22 humanized heavy chain variable region

<400> SEQUENCE: 7

```
Met Glu Leu Gly Leu Ser Trp Val Phe Leu Val Ala Ile Leu Glu Gly
1               5                   10                  15

Val Gln Cys Glu Val Gln Leu Val Glu Ser Gly Gly Gly Leu Val Gln
                20                  25                  30
```

```
Pro Gly Gly Ser Leu Arg Leu Ser Cys Ala Ala Ser Glu Tyr Glu Phe
            35                  40                  45

Pro Ser His Asp Met Ser Trp Val Arg Gln Ala Pro Gly Lys Gly Leu
    50                  55                  60

Glu Trp Val Ser Ala Ile Thr Ser Asp Gly Ile Ser Thr Tyr Tyr Pro
65                  70                  75                  80

Asp Thr Met Glu Arg Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg His Asp Trp Asp Glu Gly Phe Ala Ser Trp Gly
            115                 120                 125

Gln Gly Thr Leu Val Thr Val Ser Ser Ala Ser Thr Lys Gly Pro Ser
        130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro
            165                 170
```

<210> SEQ ID NO 8
<211> LENGTH: 171
<212> TYPE: PRT
<213> ORGANISM: Artificial Sequence
<220> FEATURE:
<223> OTHER INFORMATION: H1-LA22 humanized heavy chain variable region

<400> SEQUENCE: 8

```
Met Glu Leu Gly Leu Ser Trp Val Phe Leu Val Ala Ile Leu Glu Gly
1               5                   10                  15

Val Gln Cys Glu Val Gln Leu Val Glu Ser Gly Gly Gly Leu Val Gln
            20                  25                  30

Pro Gly Gly Ser Leu Arg Leu Ser Cys Glu Ser Asn Glu Tyr Glu Phe
            35                  40                  45

Pro Ser His Asp Met Ser Trp Val Arg Gln Ala Pro Gly Lys Gly Leu
    50                  55                  60

Glu Trp Val Ser Ala Ile Thr Ser Asp Gly Ile Ser Thr Tyr Tyr Pro
65                  70                  75                  80

Asp Thr Met Glu Arg Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg His Asp Trp Asp Glu Gly Phe Ala Ser Trp Gly
            115                 120                 125

Gln Gly Thr Leu Val Thr Val Ser Ser Ala Ser Thr Lys Gly Pro Ser
        130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro
            165                 170
```

<210> SEQ ID NO 9
<211> LENGTH: 171
<212> TYPE: PRT
<213> ORGANISM: Artificial Sequence
<220> FEATURE:
<223> OTHER INFORMATION: H2-LA22 humanized heavy chain variable region

<400> SEQUENCE: 9

```
Met Glu Leu Gly Leu Ser Trp Val Phe Leu Val Ala Ile Leu Glu Gly
1               5                   10                  15

Val Gln Cys Glu Val Gln Leu Val Glu Ser Gly Gly Gly Leu Val Gln
            20                  25                  30

Pro Gly Gly Ser Leu Arg Leu Ser Cys Glu Ser Asn Glu Tyr Glu Phe
        35                  40                  45

Pro Ser His Asp Met Ser Trp Val Arg Gln Ala Pro Gly Lys Gly Leu
    50                  55                  60

Glu Trp Val Ser Ala Ile Thr Ser Asp Gly Ile Ser Thr Tyr Tyr Pro
65                  70                  75                  80

Asp Thr Met Glu Arg Arg Phe Thr Ile Ser Arg Asp Asn Thr Lys Lys
                85                  90                  95

Thr Leu Tyr Leu Gln Met Asn Ser Leu Arg Ala Glu Asp Thr Ala Val
            100                 105                 110

Tyr Tyr Cys Ala Arg His Asp Trp Asp Glu Gly Phe Ala Ser Trp Gly
            115                 120                 125

Gln Gly Thr Leu Val Thr Val Ser Ser Ala Ser Thr Lys Gly Pro Ser
        130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro
            165                 170

<210> SEQ ID NO 10
<211> LENGTH: 171
<212> TYPE: PRT
<213> ORGANISM: Artificial Sequence
<220> FEATURE:
<223> OTHER INFORMATION: H3-LA22 humanized heavy chain variable region

<400> SEQUENCE: 10

Met Glu Leu Gly Leu Ser Trp Val Phe Leu Val Ala Ile Leu Glu Gly
1               5                   10                  15

Val Gln Cys Glu Val Gln Leu Val Glu Ser Gly Gly Gly Leu Val Gln
            20                  25                  30

Pro Gly Gly Ser Leu Arg Leu Ser Cys Ala Ser Asn Glu Tyr Glu Phe
        35                  40                  45

Pro Ser His Asp Met Ser Trp Val Arg Gln Thr Pro Gly Lys Gly Leu
    50                  55                  60

Glu Trp Val Ser Ala Ile Thr Ser Asp Gly Ile Ser Thr Tyr Tyr Pro
65                  70                  75                  80

Asp Thr Met Glu Arg Arg Phe Thr Ile Ser Arg Asp Asn Ser Lys Asn
                85                  90                  95

Thr Leu Tyr Leu Gln Met Ser Ser Leu Arg Ala Glu Asp Thr Ala Val
            100                 105                 110

Tyr Tyr Cys Ala Arg His Asp Trp Asp Glu Gly Phe Ala Ser Trp Gly
            115                 120                 125

Gln Gly Thr Leu Val Thr Val Ser Ser Ala Ser Thr Lys Gly Pro Ser
        130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro
            165                 170

<210> SEQ ID NO 11
```

```
<211> LENGTH: 171
<212> TYPE: PRT
<213> ORGANISM: Artificial Sequence
<220> FEATURE:
<223> OTHER INFORMATION: H4-LA22 humanized heavy chain variable region

<400> SEQUENCE: 11

Met Glu Leu Gly Leu Ser Trp Val Phe Leu Val Ala Ile Leu Glu Gly
1               5                   10                  15

Val Gln Cys Glu Val Gln Leu Val Glu Ser Gly Gly Gly Leu Val Gln
            20                  25                  30

Pro Gly Gly Ser Leu Arg Leu Ser Cys Ala Ser Asn Glu Tyr Glu Phe
        35                  40                  45

Pro Ser His Asp Met Ser Trp Val Arg Gln Thr Pro Gly Lys Arg Leu
    50                  55                  60

Glu Trp Val Ser Ala Ile Thr Ser Asp Gly Ile Ser Thr Tyr Tyr Pro
65                  70                  75                  80

Asp Thr Met Glu Arg Arg Phe Thr Ile Ser Arg Asp Asn Ser Lys Asn
                85                  90                  95

Thr Leu Tyr Leu Gln Met Ser Ser Leu Arg Ala Glu Asp Thr Ala Val
            100                 105                 110

Tyr Tyr Cys Ala Arg His Asp Trp Asp Glu Gly Phe Ala Ser Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro
                165                 170

<210> SEQ ID NO 12
<211> LENGTH: 132
<212> TYPE: PRT
<213> ORGANISM: Artificial Sequence
<220> FEATURE:
<223> OTHER INFORMATION: h0-LA22 humanized light chain variable region

<400> SEQUENCE: 12

Met Arg Leu Pro Ala Gln Leu Leu Gly Leu Leu Met Leu Trp Val Pro
1               5                   10                  15

Gly Ser Ser Gly Asp Val Val Met Thr Gln Ser Pro Leu Ser Leu Pro
            20                  25                  30

Val Thr Leu Gly Gln Pro Ala Ser Ile Ser Cys Arg Ser Ser Gln Ser
        35                  40                  45

Leu Val His Ser Asn Gly Asn Thr Tyr Leu His Trp Phe Gln Gln Arg
    50                  55                  60

Pro Gly Gln Ser Pro Arg Arg Leu Ile Tyr Lys Val Ser Asn Arg Phe
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110

Cys Ser Gln Ser Ser His Val Pro Pro Ala Phe Gly Gly Gly Thr Lys
        115                 120                 125

Leu Glu Ile Lys
    130
```

<210> SEQ ID NO 13
<211> LENGTH: 132
<212> TYPE: PRT
<213> ORGANISM: Artificial Sequence
<220> FEATURE:
<223> OTHER INFORMATION: h1-LA22 humanized light chain variable region

<400> SEQUENCE: 13

```
Met Arg Leu Pro Ala Gln Leu Leu Gly Leu Leu Met Leu Trp Val Pro
1               5                   10                  15

Gly Ser Ser Gly Asp Val Val Met Thr Gln Ser Pro Leu Ser Leu Pro
            20                  25                  30

Val Thr Leu Gly Gln Gln Ala Ser Ile Ser Cys Arg Ser Ser Gln Ser
        35                  40                  45

Leu Val His Ser Asn Gly Asn Thr Tyr Leu His Trp Phe Gln Gln Arg
    50                  55                  60

Pro Gly Gln Ser Pro Arg Leu Leu Ile Tyr Lys Val Ser Asn Arg Phe
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Phe
            100                 105                 110

Cys Ser Gln Ser Ser His Val Pro Pro Ala Phe Gly Gly Gly Thr Lys
        115                 120                 125

Leu Glu Ile Lys
    130
```

<210> SEQ ID NO 14
<211> LENGTH: 132
<212> TYPE: PRT
<213> ORGANISM: Artificial Sequence
<220> FEATURE:
<223> OTHER INFORMATION: h2-LA22 humanized light chain variable region

<400> SEQUENCE: 14

```
Met Arg Leu Pro Ala Gln Leu Leu Gly Leu Leu Met Leu Trp Val Pro
1               5                   10                  15

Gly Ser Ser Gly Asp Val Val Met Thr Gln Ser Pro Leu Ser Leu Pro
            20                  25                  30

Val Thr Leu Gly Gln Pro Ala Ser Ile Ser Cys Arg Ser Ser Gln Ser
        35                  40                  45

Leu Val His Ser Asn Gly Asn Thr Tyr Leu His Trp Tyr Gln Gln Arg
    50                  55                  60

Pro Gly Gln Ser Pro Arg Leu Leu Ile Tyr Lys Val Ser Asn Arg Phe
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Ile Tyr Phe
            100                 105                 110

Cys Ser Gln Ser Ser His Val Pro Pro Ala Phe Gly Gly Gly Thr Lys
        115                 120                 125

Leu Glu Ile Lys
    130
```

<210> SEQ ID NO 15
<211> LENGTH: 538
<212> TYPE: DNA
<213> ORGANISM: Artificial Sequence
<220> FEATURE:

<223> OTHER INFORMATION: H0-LA22 humanized heavy chain variable region

<400> SEQUENCE: 15

```
gcttggtacc atggagttgg ggctgagctg ggttttcctt gttgctatat tagaaggtgt    60
ccagtgtgag gtgcagctgg tggagtctgg gggaggcttg gtacagcctg ggggtccct   120
gagactctct tgtgaatcca atgaatacga attcccttcc catgacatgt cttgggtccg   180
ccaggctcca gggaaggggc tggagtgggt ctcagccatt actagtgatg gtattagcac   240
ctactatcca gacaccatgg agagacggtt caccatctcc agagacaatt ccaagaacac   300
gctgtatctg caaatgaaca gcctgagagc cgaggacacg gccgtgtatt actgtgcaag   360
acatgactgg gacgaggggt ttgcttcctg gggccaaggc accctggtca ccgtctcgtc   420
agcctccacc aagggcccat cggtcttccc cctggcaccc tcctccaaga gcacctctgg   480
gggcacagca gccctgggct gcctggtcaa ggactacttc cccgaaccgg tgacggtg    538
```

<210> SEQ ID NO 16
<211> LENGTH: 538
<212> TYPE: DNA
<213> ORGANISM: Artificial Sequence
<220> FEATURE:
<223> OTHER INFORMATION: H1-LA22 humanized heavy chain variable region

<400> SEQUENCE: 16

```
gcttggtacc atggagttgg ggctgagctg ggttttcctt gttgctatat tagaaggtgt    60
ccagtgtgag gtgcagctgg tggagtctgg gggaggcttg gtacagcctg ggggtccct   120
gagactctct tgtgcagcct ctgaatacga attcccttcc catgacatgt cttgggtccg   180
ccaggctcca gggaaggggc tggagtgggt ctcagccatt actagtgatg gtattagcac   240
ctactatcca gacaccatgg agagacggtt caccatctcc agagacaatt ccaagaacac   300
gctgtatctg caaatgaaca gcctgagagc cgaggacacg gccgtgtatt actgtgcaag   360
acatgactgg gacgaggggt ttgcttcctg gggccaaggc accctggtca ccgtctcgtc   420
agcctccacc aagggcccat cggtcttccc cctggcaccc tcctccaaga gcacctctgg   480
gggcacagca gccctgggct gcctggtcaa ggactacttc cccgaaccgg tgacggtg    538
```

<210> SEQ ID NO 17
<211> LENGTH: 538
<212> TYPE: DNA
<213> ORGANISM: Artificial Sequence
<220> FEATURE:
<223> OTHER INFORMATION: H2-LA22 humanized heavy chain variable region

<400> SEQUENCE: 17

```
gcttggtacc atggagttgg ggctgagctg ggttttcctt gttgctatat tagaaggtgt    60
ccagtgtgag gtgcagctgg tggagtctgg gggaggcttg gtacagcctg ggggtccct   120
gagactctct tgtgaatcca atgaatacga attcccttcc catgacatgt cttgggtccg   180
ccaggctcca gggaaggggc tggagtgggt ctcagccatt actagtgatg gtattagcac   240
ctactatcca gacaccatgg agagacggtt caccatctcc agagacaata ccaagaagac   300
gctgtatctg caaatgaaca gcctgagagc cgaggacacg gccgtgtatt actgtgcaag   360
acatgactgg gacgaggggt ttgcttcctg gggccaaggc accctggtca ccgtctcgtc   420
agcctccacc aagggcccat cggtcttccc cctggcaccc tcctccaaga gcacctctgg   480
gggcacagca gccctgggct gcctggtcaa ggactacttc cccgaaccgg tgacggtg    538
```

<210> SEQ ID NO 18
<211> LENGTH: 538
<212> TYPE: DNA
<213> ORGANISM: Artificial Sequence
<220> FEATURE:
<223> OTHER INFORMATION: H3-LA22 humanized heavy chain variable region

<400> SEQUENCE: 18

```
gcttggtacc atggagttgg ggctgagctg ggttttcctt gttgctatat tagaaggtgt      60
ccagtgtgag gtgcagctgg tggagtctgg gggaggcttg gtacagcctg gggggtccct     120
gagactctct tgtgcatcca atgaatacga attcccttcc catgacatgt cttgggtccg     180
ccagactcca gggaaggggc tggagtgggt ctcagccatt actagtgatg gtattagcac     240
ctactatcca gacaccatgg agagacggtt caccatctcc agagacaatt ccaagaacac     300
gctgtatctg caaatgagca gcctgagagc cgaggacacg gccgtgtatt actgtgcaag     360
acatgactgg gacgaggggt tgcttcctg gggccaaggc accctggtca ccgtctcgtc      420
agcctccacc aagggcccat cggtcttccc cctggcaccc tcctccaaga gcacctctgg     480
gggcacagca gccctgggct gcctggtcaa ggactacttc cccgaaccgg tgacggtg      538
```

<210> SEQ ID NO 19
<211> LENGTH: 538
<212> TYPE: DNA
<213> ORGANISM: Artificial Sequence
<220> FEATURE:
<223> OTHER INFORMATION: H4-LA22 humanized heavy chain variable region

<400> SEQUENCE: 19

```
gcttggtacc atggagttgg ggctgagctg ggttttcctt gttgctatat tagaaggtgt      60
ccagtgtgag gtgcagctgg tggagtctgg gggaggcttg gtacagcctg gggggtccct     120
gagactctct tgtgcatcca atgaatacga attcccttcc catgacatgt cttgggtccg     180
ccagactcca gggaagagc tggagtgggt ctcagccatt actagtgatg gtattagcac      240
ctactatcca gacaccatgg agagacggtt caccatctcc agagacaatt ccaagaacac     300
gctgtatctg caaatgagca gcctgagagc cgaggacacg gccgtgtatt actgtgcaag     360
acatgactgg gacgagggt tgcttcctg gggccaaggc accctggtca ccgtctcgtc       420
agcctccacc aagggcccat cggtcttccc cctggcaccc tcctccaaga gcacctctgg     480
gggcacagca gccctgggct gcctggtcaa ggactacttc cccgaaccgg tgacggtg      538
```

<210> SEQ ID NO 20
<211> LENGTH: 423
<212> TYPE: DNA
<213> ORGANISM: Artificial Sequence
<220> FEATURE:
<223> OTHER INFORMATION: h0-LA22 humanized light chain variable region

<400> SEQUENCE: 20

```
gcttggtacc atgaggctcc ctgctcagct cctggggctg ctaatgctct gggtcccagg      60
atccagtggg gatgttgtga tgactcagtc tccactctcc ctgcccgtca cccttggaca     120
gccggcctcc atctcctgca gatctagtca gagccttgta cacagtaatg gaaacaccta     180
tttacattgg tttcagcaga ggccaggcca atctccaagg cgcctaattt ataaagtttc     240
caaccgattt tctggggtcc cagacagatt cagcggcagt gggtcaggca ctgatttcac     300
actgaaaatc agcagggtgg aggctgagga tgttggggtt tattactgct ctcaaagttc     360
acatgttcct ccggcgttcg gcggagggac caagctggag atcaaacgta agtctcgagt     420
``` ctc                                                                    423

<210> SEQ ID NO 21
<211> LENGTH: 423
<212> TYPE: DNA
<213> ORGANISM: Artificial Sequence
<220> FEATURE:
<223> OTHER INFORMATION: h1-LA22 humanized light chain variable region

<400> SEQUENCE: 21
gcttggtacc atgaggctcc ctgctcagct cctggggctg ctaatgctct gggtcccagg      60
atccagtggg gatgttgtga tgactcagtc tccactctcc ctgcccgtca cccttggaca     120
gcaggcctcc atctcctgca gatctagtca gagccttgta cacagtaatg gaaacaccta    180
tttacattgg tttcagcaga ggccaggcca atctccaagg ctcctaattt ataaagtttc    240
caaccgattt tctggggtcc cagacagatt cagcggcagt gggtcaggca ctgatttcac    300
actgaaaatc agcagggtgg aggctgagga tgttggggtt tatttctgct ctcaaagttc    360
acatgttcct ccggcgttcg gcggagggac caagctggag atcaaacgta agtctcgagt    420
ctc                                                                   423

<210> SEQ ID NO 22
<211> LENGTH: 423
<212> TYPE: DNA
<213> ORGANISM: Artificial Sequence
<220> FEATURE:
<223> OTHER INFORMATION: h3-LA22 humanized light chain variable region

<400> SEQUENCE: 22
gcttggtacc atgaggctcc ctgctcagct cctggggctg ctaatgctct gggtcccagg      60
atccagtggg gatgttgtga tgactcagtc tccactctcc ctgcccgtca cccttggaca     120
gccggcctcc atctcctgca gatctagtca gagccttgta cacagtaatg gaaacaccta    180
tttacattgg tatcagcaga ggccaggcca atctccaagg ctcctaattt ataaagtttc    240
caaccgattt tctggggtcc cagacagatt cagcggcagt gggtcaggca ctgatttcac    300
actgaaaatc agcagggtgg aggctgagga tgttgggatt tatttctgct ctcaaagttc    360
acatgttcct ccggcgttcg gcggagggac caagctggag atcaaacgta agtctcgagt    420
ctc                                                                   423

<210> SEQ ID NO 23
<211> LENGTH: 34
<212> TYPE: DNA
<213> ORGANISM: Artificial Sequence
<220> FEATURE:
<223> OTHER INFORMATION: humanized

<400> SEQUENCE: 23
tgaggagacg gtgaccgtgg tcccttggcc ccag                                  34

<210> SEQ ID NO 24
<211> LENGTH: 22
<212> TYPE: DNA
<213> ORGANISM: Artificial Sequence
<220> FEATURE:
<223> OTHER INFORMATION: humanized

<400> SEQUENCE: 24
aggtsmarct gcagsagtcw gg                                               22

```
<210> SEQ ID NO 25
<211> LENGTH: 22
<212> TYPE: DNA
<213> ORGANISM: Artificial Sequence
<220> FEATURE:
<223> OTHER INFORMATION: humanized

<400> SEQUENCE: 25
gttagatctc cagcttggtc cc                                              22

<210> SEQ ID NO 26
<211> LENGTH: 24
<212> TYPE: DNA
<213> ORGANISM: Artificial Sequence
<220> FEATURE:
<223> OTHER INFORMATION: humanized

<400> SEQUENCE: 26
gacattcagc tgacccagtc tcca                                            24
```

HUMANIZED ANTI-HUMAN EPIDERMAL GROWTH FACTOR RECEPTOR ANTIBODY AND APPLICATION THEREOF

TECHNICAL FIELD

The present invention relates to humanization of anti-Epidermal Growth Factor Receptor (EGFR) antibodies and applications of using the same for treating cancers and other human diseases.

BACKGROUND

EGF receptor belongs to a family of erbB genes and its amplification and overexpression have been observed in a high percentage of primary human carcinomas of epithelial origin including cancers of the breast, colon, lung, head and neck, kidney, prostate and bladder, and played very important roles in cancer progression. It has been shown that anti-EGFR antibodies can block the binding of EGF to EGFR and the signal transduction in the cells, inhibit tumor progression in cancer patients. Several monoclonal anti-EGFR antibodies have proven effective in treatment of human patients in clinic. In 2005, Erbitux, a humanized mouse anti-EGFR monoclonal antibody was launched as the therapy for head and neck cancer by ImClone. In 2009, another humanized anti-EGFR monoclonal antibody was launched in China for the same indication by a Chinese Biopharmaceutical.

This invention is about the humanization of another mouse anti-EGFR monoclonal antibody, designed as clone LA22, which binds to different epitopes from the one recognized by Erbitux. It has been reported previously that once binds to the EGFR on the tumor cell surface, in the absence or presence of EGF, LA22 will internalize rather quickly, and can be an ideal candidate for antibody drug conjugate.

SUMMARY OF THE INVENTION

The present invention provides the humanized anti-EGFR antibodies and methods of using the same for suppressing the growth of tumor cells and for treating cancers of epithelial origin. In one aspect, the present invention features EGFR-binding molecules and their DNA and amino acid sequences. Each molecule comprises the CDRs from mouse anti-EGFR monoclonal antibody LA22 and the FRs and Fcs from different human origins. In one embodiment, an EGFR-binding molecule of the present invention is a monoclonal antibody conjugated with a cytotoxic agent.

The present invention features EGFR-binding molecules are humanized anti-EGFR monoclonal antibodies with the amino acid sequences from the variable regions (Fv) of mouse anti-EGFR LA22 antibody, and the constant regions (Fc) of human IgGs. The Fv amino acid sequence of heavy chain of mouse monoclonal antibody LA22 is shown in SEQ ID NO.1 and the Fv amino acid sequence of light chain of mouse monoclonal antibody LA22 is shown in SEQ ID NO.2. The humanization is using the human FRs to replace the mouse FRs.

The present invention also provides one example of using the Fc amino acid sequence of human IgG1 to replace the Fc amino acid sequence of mouse LA22 first, then to modify the FRs amino acid sequences of mouse LA22 with various human FRs amino acid sequences to obtain humanized antibodies with good affinity to EGFR and high biological activity.

The present invention features humanized anti-EGFR antibodies with one of the amino acid sequences of heavy chains shown in SEQ ID NO. 7~11, and one of the amino acid sequences of light chains shown in SEQ ID NO. 12~14.

The present invention features humanized anti-EGFR antibodies with any one of the amino acid sequences of heavy chains shown in SEQ ID NO. 7~11, and the amino acid sequences of light chain shown in SEQ ID NO. 14 (light chain h2).

The present invention features humanized anti-EGFR antibodies with the amino acid sequences of heavy chains shown in SEQ ID NO. 10 (heavy chain H3), and any of the amino acid sequences of light chains shown in SEQ ID NO. 12~14.

Furthermore, the present invention features humanized anti-EGFR antibody with the amino acid sequences of heavy chain shown in SEQ ID NO. 10 (heavy chain H3), and the amino acid sequence of light chain shown in SEQ ID NO. 14 (light chain h2).

The present invention features humanized anti-EGFR antibodies with one of the DNA sequences of heavy chains shown in SEQ ID NO.15~19, and one of the DNA sequences of light chains shown in SEQ ID NO. 20~22.

Furthermore, the present invention features humanized anti-EGFR antibody with the DNA sequence of heavy chain shown in SEQ ID NO. 18 (heavy chain H3), and the DNA sequence of light chain shown in SEQ ID NO. 22 (light chain h2).

The present invention features the expression plasmid containing the humanized anti-EGFR antibody sequences.

The present invention also covers the plasmid, the host cells containing the humanized anti-EGFR antibody sequences.

The invention also provides humanized anti-EGFR antibodies for treatment of human diseases targeting EGFR.

The EGFR-binding molecules or antibodies of the present invention can be used to kill or inhibit the growth of cancer cells. These methods comprise contacting cancer cells with an EGFR-binding molecule or antibody of the present invention.

In addition, the EGFR-binding molecules or antibodies of the present invention can be used to treat cancers. These methods comprise administrating an effective amount of an EGFR-binding molecule or antibody of the present invention to a subject in need thereof. Cancers or cancer cells amenable to the present invention include those of epithelial origin.

Furthermore, the present invention also features pharmaceutical compositions comprising an EGFR-binding molecule or antibody of the present invention.

The present invention provides the primer sequences for light and heavy chains as follow:

```
VH1FOR:
TGAGGAGACGGTGACCGTGGTCCCTTGGCCCCAG

VH1BACK:
AGGTSMARCTGCAGSAGTCWGG

VK1FOR:
GTTAGATCTCCAGCTTGGTCCC

VK1BACK:
GACATTCAGCTGACCCAGTCTCCA
```

The present invention provides the method of humanization of anti-EGFR monoclonal antibody, including:

Total RNA was extracted from hybridoma cells of mouse anti-EGFR monoclonal antibody LA22, then reverse transcribed into the cDNA using VH1FOR and VK1FOR as the primers for variable regions of heavy chain and light chain to obtain the cDNAs library. Use this cDNA library as the template for PCR amplification with the primers VH1FOR and VH1BACK for heavy chain variable region of mouse monoclonal antibody LA22, and primers VK1FOR and VK1BACK for the light chain variable region. Purify the PCR products of interested, perform subcloning and transformed into competent cells, then screening positive clones by DNA sequencing.

Once the variable region sequences confirmed, chemically synthesize both the variable sequences with artificially added restriction enzyme sites (Kpn I and Xho I for light chain variable region, KpnI and AgeI for heavy chain variable region), ligate to vector pJH16-H39E3.L1kappa and pJH16 to obtain the expression plasmids for heavy chain and light chain chimeric antibody. Screen for positive clones after transformation by sequencing and restriction enzyme digestions.

Using the known human antibody frame works (FRs) as the replacing sequences for the mouse LA22's, together with 3D modeling and immunogenicity prediction softwares, we designed 5 humanized heavy chain variable region sequences (amino acid sequences are shown in SEQ ID NO.7~11, the nucleotide sequence as shown in SEQ ID NO.15~19) and 3 humanized light chain variable region sequences (amino acid sequences are shown in SEQ ID NO.12~14, the nucleotide sequence as shown in SEQ ID NO.20 to 22).

Chemically synthesize both the rariable sequences with artificially added restriction enzyme sites (Kpn I and Xho I for light chain variable region, KpnI and AgeI for heavy chain variable region), ligate to vector pJH16-H39E3.L1kappa and pJH16 to obtain the expression plasmids for heavy chain and light chain humanized antibodies. Screen for positive clones after transformation by sequencing and restriction enzyme digestions.

Co-transfection of the heavy and light chain chimeric antibody expression plasmids generated the mouse/human IgG1 chimeric anti-EGFR monoclonal antibody. Co-transfection of different combinations of the chimeric/humanized light and heavy chain expression plasmids produced 30 different humanized anti-EGFR monoclonal antibodies with different expression levels and affinities for EGFR.

The invention presents the humanized anti-EGFR antibodies which bind to different epitope and inhibit the tumor formation in a different way than Erbitux. In combination with Ervitux, the new humanized antiEGFR antibodies may increase the efficacy to treat cancers. Most importantly, once bound to the surface EGFR, these new anti-EGFR antibodies internalize rather quickly, which made them ideal candidate for antibody drug conjugation and other biotherapy. The invention also features method of humanization which leads to 90% of the amino acid sequences are human sequence, and significantly reduce the risk of human anti-mouse immunogenicity. The present invention also demonstrated that the humanized anti-EGFR antibodies have the affinity to EGFR in the range of 2.3 nM, which is very similar to the mouse anti-EGFR monoclonal antibody LA22.

BRIEF DESCRIPTION OF THE DRAWINGS

The drawings are provided for illustration, not limitation.

FIG. 4 Restriction digestions of the chimeric antibody expression plasmids.

FIG. 8 Example of DNA sequence confirmation of humanized antibody. H2-1 CMV is the confirmed sequence of humanized heavy chain H2, and he-LA22 is the designed sequence of humanized heavy chain H2. Alignment data shows 100% accuracy.

FIG. 9 Three humanized amino acid sequences of the light chains.

FIG. 10 Five humanized amino acid sequences of the heavy chains.

DETAILED DESCRIPTION

It should be understood that the above-described embodiments and the following examples are given by way of illustration, not limitation. Various changes and modifications within the scope of the present invention will become apparent to those skilled in the art from the present description.

Unless specified, all the techniques used are common practices and can be performed by skilled personnel. All of the materials and reagents can be purchased commercially.

Example 1 Cloning of the Variable Regions of Mouse Anti-EGFR mAb LA22

Monoclonal antibody LA22 is described in U.S. Pat. No. 5,459,061. The hybridoma LA22 is deposited at ATCC. We used a 5'RACE (Rapid amplification of cDNA ends) method to obtain the DNA sequences of the variable regions of the light and heavy chains of anti-EGFR mouse mAb LA22. The primers used in the reactions as shown below:

```
VH1FOR:
TGAGGAGACGGTGACCGTGGTCCCTTGGCCCCAG

VH1BACK:
AGGTSMARCTGCAGSAGTCWGG

VK1FOR:
GTTAGATCTCCAGCTTGGTCCC

VK1BACK:
GACATTCAGCTGACCCAGTCTCCA
```

First, VH1FOR and VK1FOR were used to obtain the cDNA library from LA22, then VH1FOR+VH1BACK were used as the pair to PCR clone out the sequence of the variable region of the heavy chain, and VK1FOR+VK1BACK for the light chain. The PCR products were subject to DNA sequencing to obtain the gene sequences.

Briefly, the total RNA from 1×10$^7$ LA22 hybridoma cells was extracted using Qiagen RNeasykit. Following the instruction of 5'-RACEkit from Transgen, VH1FOR and VK1FOR were used to obtain the cDNA library. The reaction was carried out first at 42° C., 30 min, then 85° C. for 5 min. VH1FOR+VH1BACK were used as the pair to PCR clone out the sequence of the variable region of the heavy chain, and VK1FOR+VK1BACK for the light chain. 37 cycles of PCR reactions were carried out. PCR products from different reaction were separated by agarose gel and the bands at the expected sizes (320 bp for light chain and 360 bp for heavy chain) were cut-out, extracted and cloned into pEASY-T1 (Transgen) vector. After the transfection, the DH5α *E. Coli* cells were seeded on IPTGIX-gal plates, 8 clones from each transfection were picked, expanded and sent out to GeneWiz for DNA sequencing.

The VH cDNA sequence of mouse LA22 is shown in SEQ ID NO.3, and VL cDNA in SEQ ID NO.4. The translated amino acid sequences for VH and VL of mouse LA22 are shown in SEQ ID NO.1-2.

Figure 1:
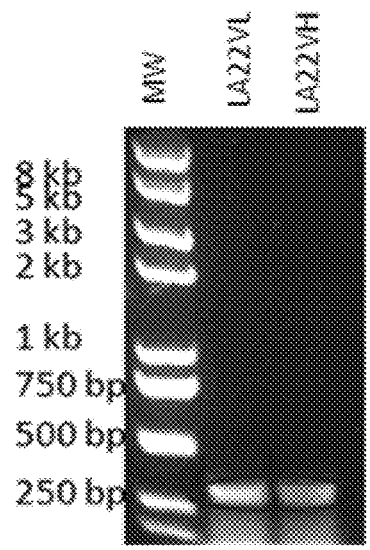
FIG. 1 Agarose gel of the regular-PCR of the VH and VL of LA22.
Figure 2:
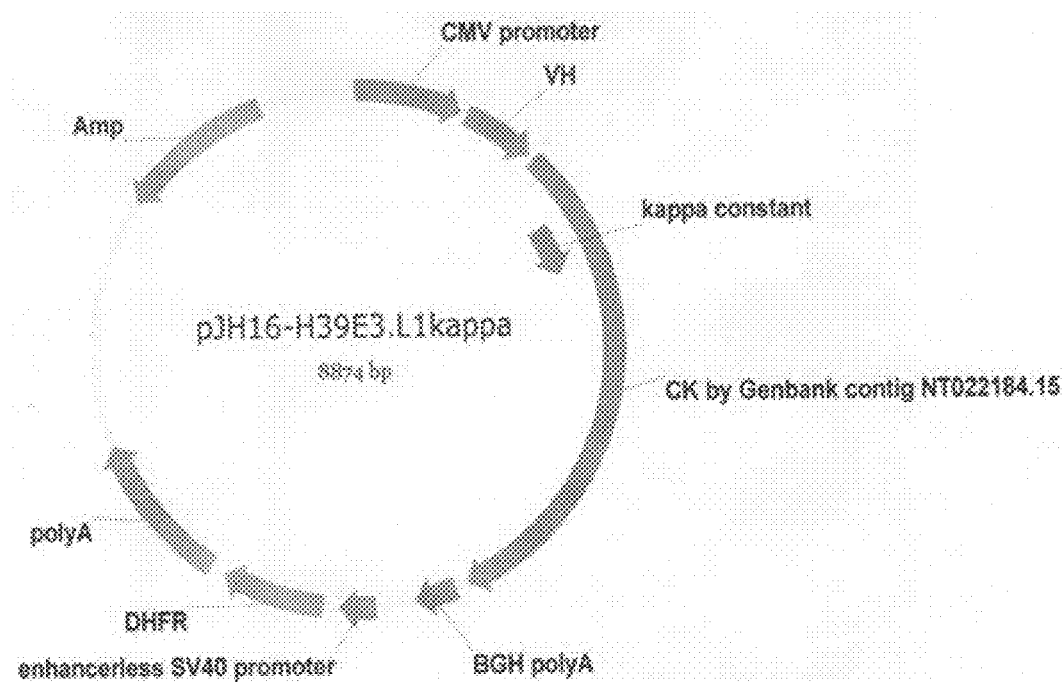
FIG. 2 Plasmid map for expression of the light chain with the constant region from human kappa.
Figure 3:
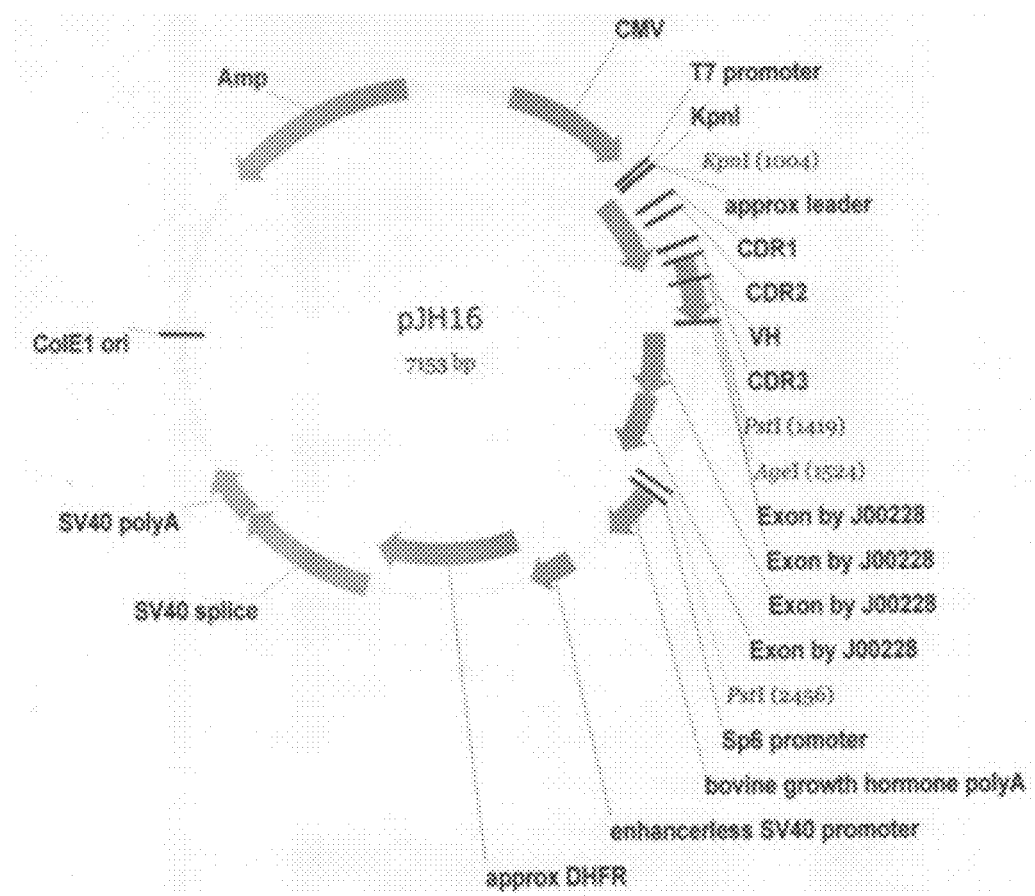
FIG. 3 Plasmid map for expression of the heavy chain with the constant region from human IgG1.
Figure 4A:
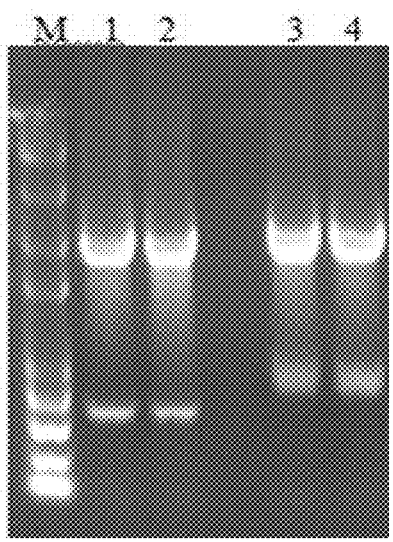
In FIG. 4a, lanes 1-2 are the bands at 450 bp, expected size of the digestion product of light chain in pUC57-LA22 by KpnI-XhoI. Lanes 3-4 are the bands at 550 bp, expected size of the digestion product of heavy chain in pUC57-LA22 by KpnI-AgeI.
Figure 4B:
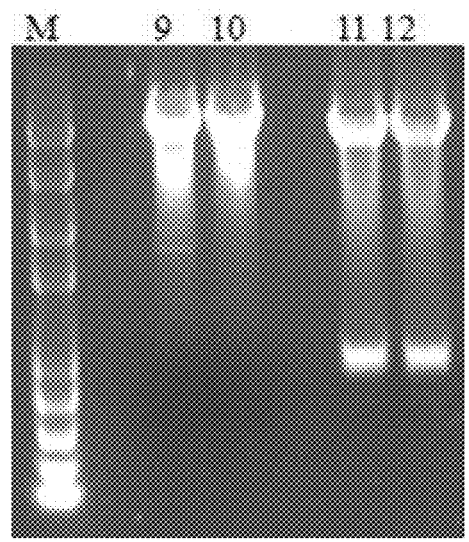
In FIG. 4b, lanes 9-10 are the bands at 450 bp, expected size of the digestion product of light chain in pJH16-H39EL1-LA22 by KpnI-XhoI. Lanes 3-4 are the bands at 550 bp, expected size of the digestion product of heavy chain in pJH16-H39EL1-LA22 by KpnI-AgeI.

Example 2 Construction of Expression Vectors for Chimeric Monoclonal Antibody According the nucleotide sequences of the monoclonal antibody LA22 heavy and light chain variable regions, the restriction sites of Kpn I and Xho I for the light chain and Kpn I with Age I for the heavy chain were added in the gene synthesis. The genes were inserted into pUC57 vectors containing constant regions of light chain kappa and heavy chain IgG1 respectively by GeneWiz. The plasmids and the expression vectors (pJH16-H39E3.L1kappa and pJH16) were subjected to enzyme digestions at 37 C overnight. Results of digestions of pUC57-LA22 light, heavy chain, and the expression vectors are shown in FIG. 4*a* and FIG. 4*b*. The bands of target genes and expression vectors were cut-out and extracted using Qiagen Gel Extraction Kit, then performed the ligations overnight using T4 DNA ligation system and transformed into *E. coli* DH5α. Colonies were picked for DNA sequencing and the alignments of sequencing data matched the designed gene 100%. The chimeric antibody heavy chain sequence is shown as SEQ ID NO.5, the chimeric antibody light chain sequence is shown as SEQ ID NO.6.

Example 3 Design of Humanized Recombinant Monoclonal Antibody VL and VH

The VL and VH of anti-EGFR mouse monoclonal antibody LA22 were humanized as shown below.

The CDRs of mouse monoclonal antibody were grafted onto human antibody variable regions to replace the CDRs of human antibodies, so the humanized antibodies will keep the antigen-binding specificity of mouse monoclonal antibody, while reducing its heterologous to human. Principle of the method is that the mouse antibody FR(s) was only replaced with human FR(s) at the regions with clear differences, using the amino acid similar with the human antibody surface residues for replacement on the basis of maintaining the activity of the antibody and reducing the heterologous. In addition, the replaced section should be limited and try to avoid the replacements which have impact on side chain size, charge, hydrophobicity, or may form hydrogen bonds thus affecting the antibody complementarity determining region (CDR) residues conformation.

This invention provides 5 humanized heavy chains designed as H0-LA22, H1-LA22, H2-LA22, H3-LA22, H4-LA22. The amino acid sequences are shown in SEQ ID NO.7~11, the nucleotide sequences are shown in SEQ ID NO.15~19. The invention also features 3 humanization light chains designed as h0-LA22, h1-LA22, h2-LA22. The amino acid sequences are shown in SEQ ID NO.12~14, the nucleotide sequence are shown in SEQ ID NO.20~22.

Figure 6:
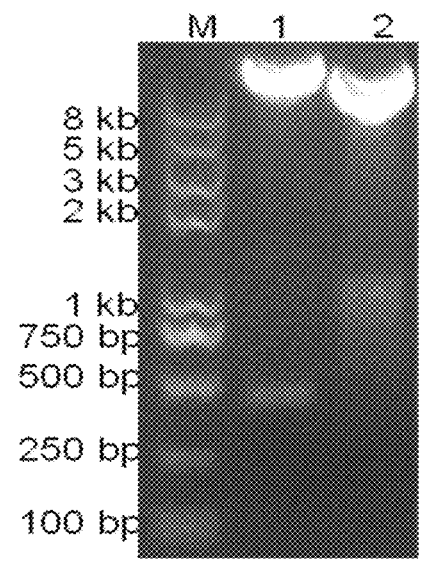
FIG. 6 Enzyme digestion of the vector. 1) 8.5 kbp, expected size from pJH16-H39E3L1 by KpnI-XhoI. 2) 7 kbp, expected size from pJH16-H39E3L1 by KpnI-AgeI.
Figure 7:
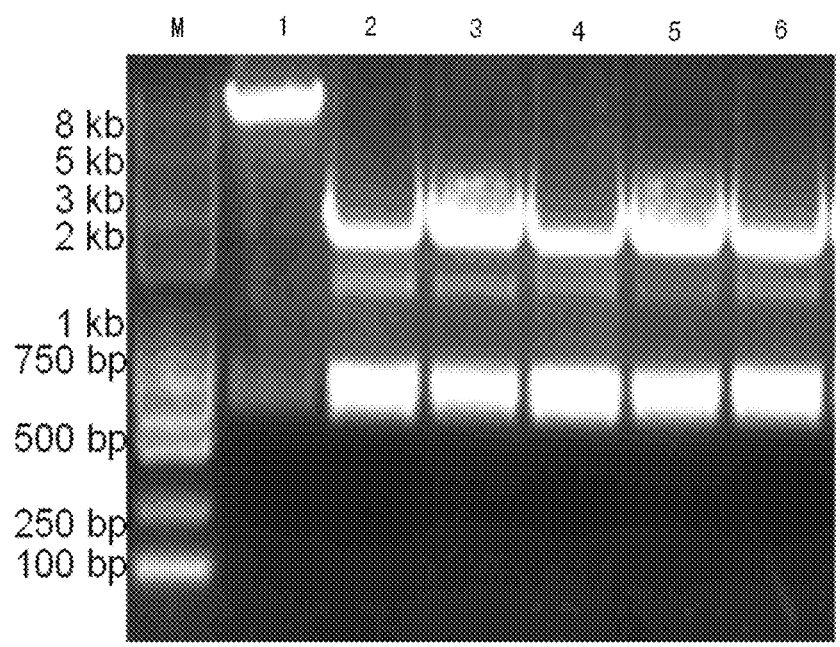
FIG. 7 Enzyme digestion of the humanized heavy chains digested by KpnI-AgeI. 1) empty vector, 2) pUC57-h0-LA22, 3) pUC57-h1-LA22, 4) pUC57-h2-LA22, 5) pUC57-h3-LA22, 6) pUC57-h4-LA22.

Example 4 Constructions of Expression Vectors for Humanized Recombinant Monoclonal Antibodies Add the restriction sites of KpnI and XhoI to the 3 humanized light chain variable region sequences obtained in Example 3, and the restriction sites of KpnI and AgeI to the 5 humanized heavy chain variable region sequences. All the light and heavy chain variable region sequences were inserted into the vector pUC57. Cut the heavy chain variable region sequences from the vector pUC57 and inserted into the corresponding sites of the expression vector pJH16 using the restriction sites of KpnI and AgeI. Cut the light chain variable region sequences from the vector pUC57 and inserted into the corresponding sites of the expression vector pJH16-H39E3.L1kappa using the restriction sites of KpnI and XhoI, to obtain the humanized recombinant monoclonal antibody heavy and light chain expression plasmids. The results of the light chain and heavy chain digestion are shown in FIG. 5, FIG. 6, and FIG. 7.

According the nucleotide sequences of the humanized monoclonal antibody LA22 heavy and light chain variable regions, the restriction sites of Kpn I and Xho I for the light chains and Kpn I with Age I for the heavy chains were added in the gene synthesis. The genes were inserted into pUC57 vectors containing constant regions of light chain kappa and heavy chain IgG1 respectively by GeneWiz. The plasmids and the expression vectors (pJH16-H39E3.L1kappa and pJH16) were subjected to enzyme digestions at 37 C overnight. Results of digestions of pUC57-LA22 light, heavy chain, and the expression vectors are shown in FIG. 4*a* and FIG. 4*b*. The bands of target genes and expression vectors were cut-out and extracted using Qiagen Gel Extraction Kit, then performed the ligations overnight using T4 DNA ligation system and transformed into E. coli DH5a. Colonies were picked for DNA sequencing and the alignments of sequencing data matched the designed gene 100%. The chimeric antibody heavy chain sequence is shown as SEQ ID NO.5, the chimeric antibody light chain sequence is shown as SEQ ID NO.6.

Figure 5:
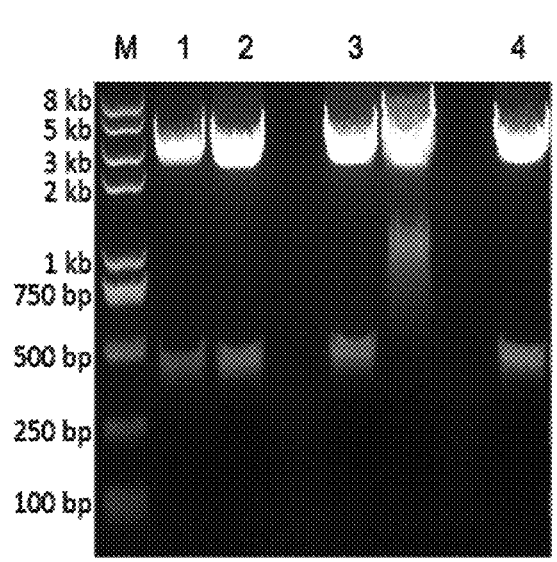
FIG. 5 Enzyme digestion of the humanized light chains. Lanes 1-2 are the bands at 450 bp, expected size from pUC57-h0-LA22 by KpnI-XhoI. Lanes 3-4 are the bands at 450 bp, expected size from pUC57-h1-LA22 by KpnI-XhoI. Lanes 5-6 are the bands at 450 bp, expected size from pUC57-h2-LA22 by KpnI-XhoI.
Figure 8:
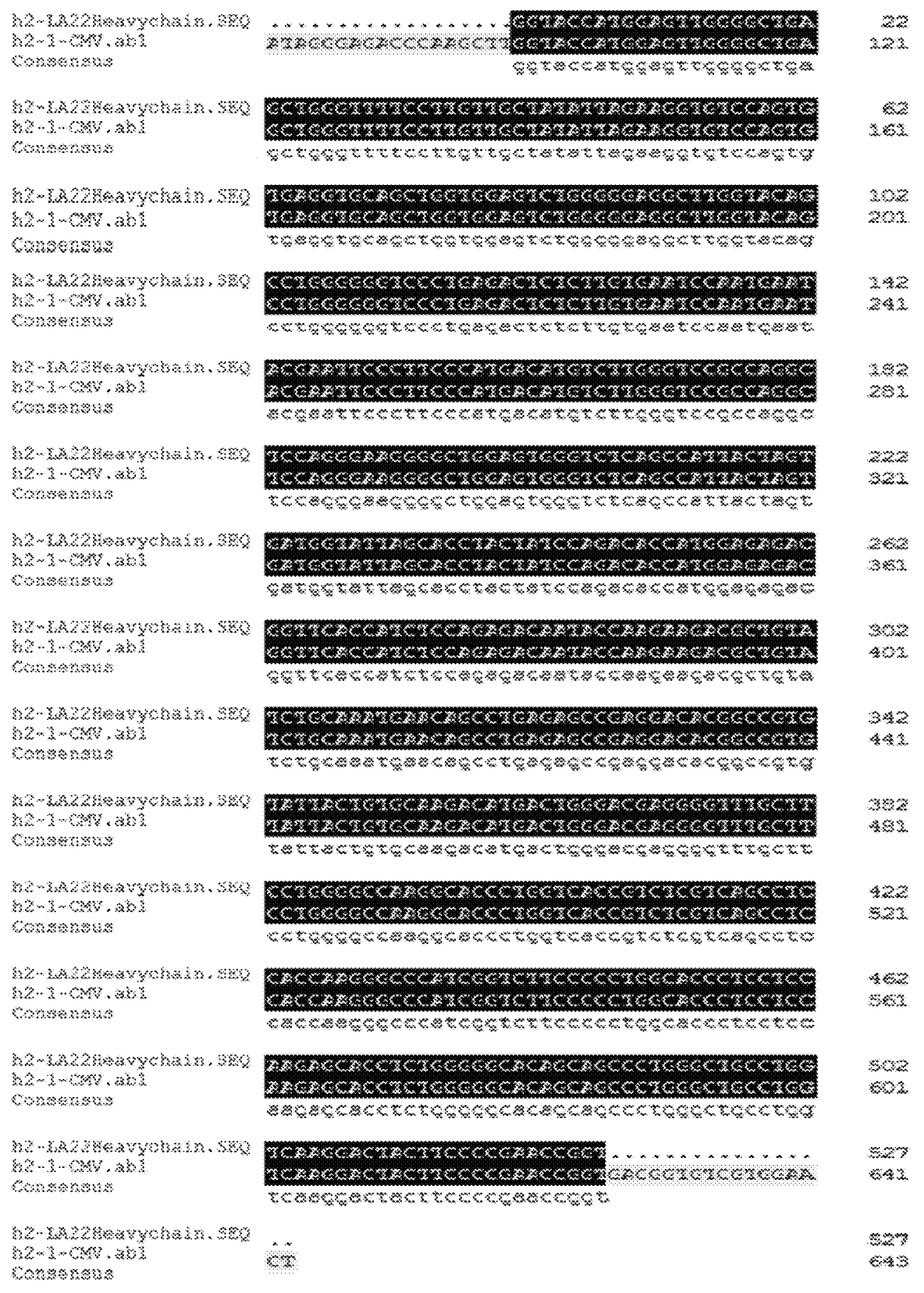

Cut the gels containing the fragments of ho/h1/h2-LA22 with the expected size of 430 bp in lane 1~4 shown in FIG. 5. Cut the gels containing the fragment of pJH16-H39E3.L1kappa in lane 1 with the expected size of 8.5 kb and the fragment of pJH16 in lane 2 with the expected size of 7 kb shown in FIG. 6. Cut the gels containing the fragment of H0/H1/H2/H3/H4-LA22 heavy chain in lane 2, 3, 4, 5, 6 with the expected size of 550 bp shown in FIG. 7, while gel extracted the fragment pJH16 in lane 1 with the expected size of 7 kb. The DNA fragments above were obtained using Qiagen Gel Extraction Kit and performed the ligation overnight using T4 DNA ligation system and then transformed into E. coli DH5α. The alignment of sequencing data was 100% correct indicating that the humanized antibody expression vectors were constructed successfully, as shown in FIG. 8.

Example 5 Expression and Purification of Humanized Recombinant Anti-EGFR Antibody The pJH16-LA22 heavy chain and light chain chimeric antibody expression vector constructed in Example 2 and the pJH16-LA22 heavy chain and light chain humanized antibody expression vector constructed in Example 4 were transformed into E. coli DH5a and cultured in 100 ml LB medium following a conventional method. Plasmid DNA were harvested from the cultures using a Qiagen Plasmid DNA UltraPure Purification kit. The purified plasmid DNAs were co-transfected into CHO or 293F cells (purchased from Invitrogen) using the Invitrogen liposome transfection kit, following the manufacturer's operating instructions.

A total of 20 different combinations of light and heavy chain plasmids were co-transfected into 293F cells. 3 days later, the culture supernatant was harvested and added to the 96 well plates pre-coated with EGFR. Preliminary evaluated the EGFR binding activity of antibody secreted using indirect ELISA (Table 1).

TABLE 1

ELISA of different combinations of H + L chains

| H0+ h2 | H1+ h2 | H2+ h2 | H3+ h2 | H4+ h2 | C1+ h2 | Chimeric LA22 | NC |
|---|---|---|---|---|---|---|---|
| 0.291 | 0.305 | 0.281 | 0.631 | 0.296 | 0.475 | 0.351 | 0.108 |
| 0.323 | 0.344 | 0.311 | 0.721 | 0.283 | 0.533 | 0.391 | 0.104 |

Heavy chain: H0+, H1+, H2+, H3+, H4+, C1+ (chimeric)
Light chain: h2
NC, negative control: antibody diluent as $1^{st}$ Ab Stable Expression CHO cells was electro-transfected and selected under MTX pressure (purchased from Sigma) in the selective Opti-CHO medium (purchased from Invitrogen). Three selecting gradients were set as 50 nM, 100 nM and 250 nM. After each round, the expression levels of IgG in the culture supernatants on Day 7 were examined using sandwich ELISA method. When the process was complete, limiting dilution was performed for monoclonal cloning. Cells were seeded at 96-well plate and cultured at 37° C. 5% $CO_2$. 14 days later, 50 μl of supernatant was collected for antibody production testing using sandwich ELISA method. Clones with better expressing results were selected for further expansion. The results showed that the combinations of different heavy chains with light chain h2 and stable expression was observed but with different levels (Table 2).

TABLE 2

The expression of humanized antibodies with different heavy chains to light chain h2

| Human IgG concentration (ng/ml) | Standard human IgG OD450 nm | | | Supernatants (1:100 dilution) OD450 nm | |
|---|---|---|---|---|---|
| 100 | 2.428 | 2.752 | H0+ h2 | 1.775 | 2.117 |
| 30 | 1.581 | 1.329 | H1+ h2 | 2.226 | 2.488 |
| 10 | 0.809 | 0.727 | H2+ h2 | 1.072 | 1.622 |
| 3 | 0.309 | 0.282 | H3+ h2 | 1.009 | 0.929 |
| 1 | 0.16 | 0.148 | H4+ h2 | 0.746 | 0.952 |
| 0.3 | 0.087 | 0.084 | NC | 0.049 | 0.051 |
| NC | 0.051 | 0.069 | NC | 0.059 | 0.054 |
|  | 0.036 | 0.038 | NC | 0.062 | 0.061 |

Figure 11:
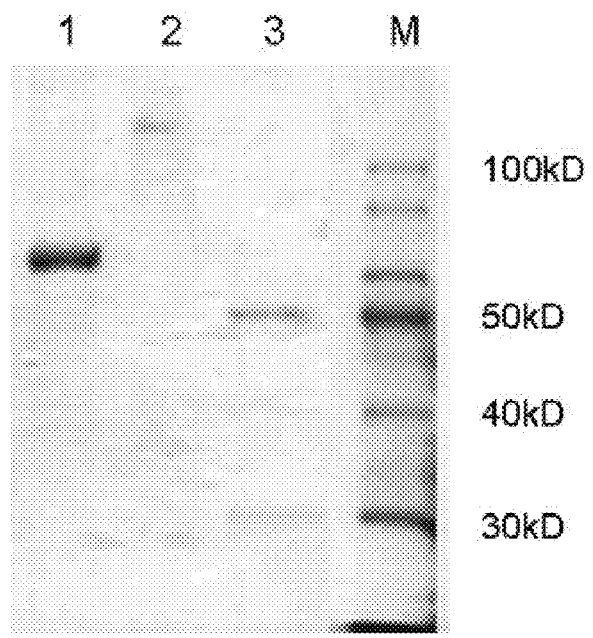
FIG. 11 SDS-PAGE and Comm-Blue Staining of humanized anti-EGFR antibody. M) MW markers, 1) BSA, 2) purified antibody under non-reducing condition, 3) purified antibody under reduced condition.

Heavy chain: H0+, H1+, H2+, H3+, H4+
Light chain: h2
NC, negative control: antibody diluent as $1^{st}$ Ab Antibody purification: Used a Protein A affinity chromatography column to purify the culture supernatant of the five stable cell lines and obtained the present invention of humanized monoclonal antibodies. The results of SDS-PAGE show that the product purity is greater than 90% (FIG. 11).

Example 6 Biological Activity Evaluation of Humanized Recombinant Anti-EGFR Antibody 1. Biacore assay. To test the affinity between human epidermal factor receptor (EGFR) and the present invention of humanized anti-EGFR antibody using BIAcore system which is based on the surface plasmon resonance technique, the chip was coated with ECD of rec. EGFR. As shown in Table 3, the binding ability of mLA22 is 2 nM, and hLA22 is 2.3 nM, both reached $10^{-9}$, indicating that some of the humanized anti-EGFR antibodies in the present invention have the same affinities as the mouse anti-EGFR antibody.

TABLE 3

Humanized anti-EGFR antibody affinity test

| Antibody | $K_{on}$ ($10^4$ $M^{-1}S^{-1}$) | $K_{off}$ ($10^{-4}$ $S^{-1}$) | $K_d$ (nM) |
|---|---|---|---|
| Mouse monoclonal antibody LA22 | 2.2 ± 0.1 | 0.43 ± 0.03 | 2.0 ± 0.01 |
| Humanized LA22 (H3 + h2) | 1.64 ± 0.29 | 0.38 ± 0.03 | 2.3 ± 0.05 |
| Humanized LA22 (H0 + h2) | 0.52 ± 0.04 | 0.69 ± 0.03 | 13.2 ± 0.02 |
| Humanized LA22 (H1 + h2) | 1.04 ± 0.08 | 1.46 ± 0.13 | 14.0 ± 0.08 |
| Humanized LA22 (H2 + h2) | 0.64 ± 0.09 | 0.77 ± 0.03 | 12.0 ± 0.05 |
| Humanized LA22 (H4 + h2) | 1.22 ± 0.09 | 1.88 ± 0.17 | 15.4 ± 0.09 |

Figure 12:
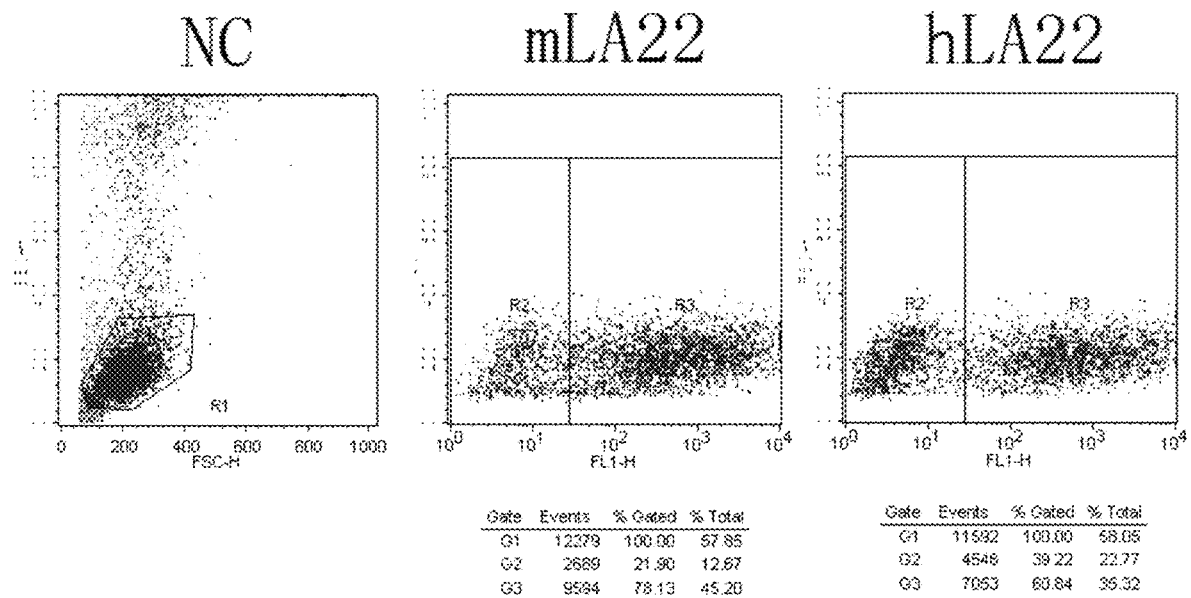
FIG. 12 FACS of A431 cells with mouse LA22 and humanized LA22. Data showed hLA22 bind to the live cell surface of A431.

2. Flow cytometric analysis. A431 cells, a human epidermoid carcinoma cell line (ATCC No. CRL-1551), were incubated with 20 μg/ml of mLA22 or hLA22 at 4° C. 60 minutes later, FITC-labeled anti-mouse or anti-human secondary antibody (Jackson Lab) were added and incubated at 4° C. for 60 min, and then subjected to flow cytometry. The results showed that mLA22 and hLA22 (the combination of light chain h2 and heavy chain H3) bind to the EGFR on live A431 cell surface in a very similar intensities (FIG. 12).

Figure 13:
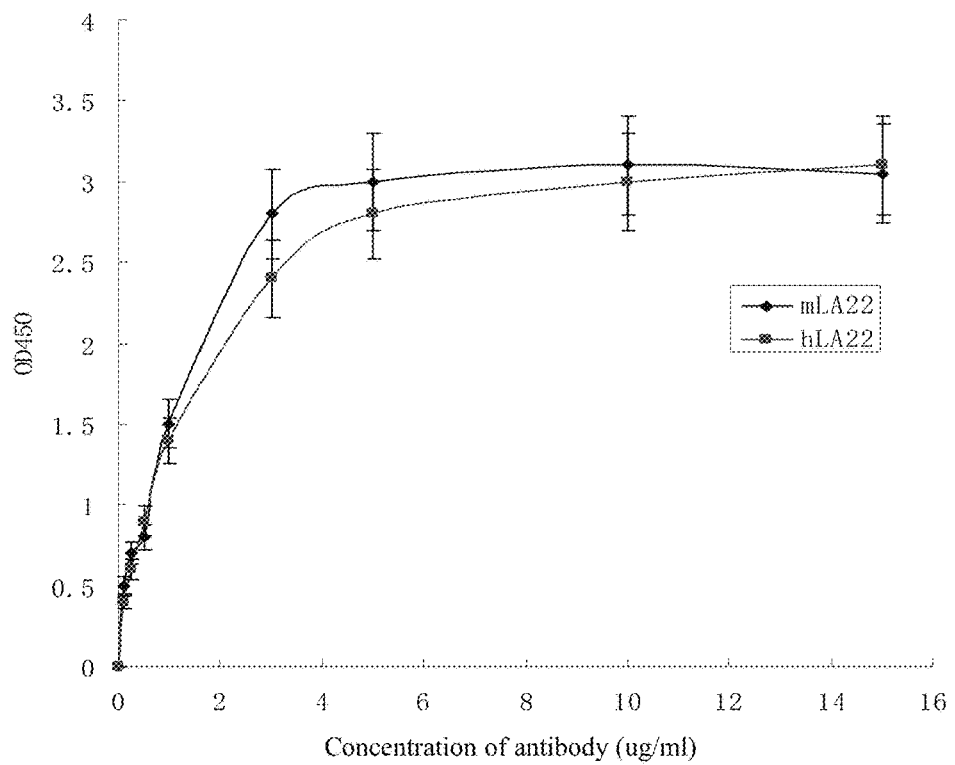
FIG. 13 Cell-based ELISA. Data showed hLA22 bind to the cell surface of A431.
Figure 14:
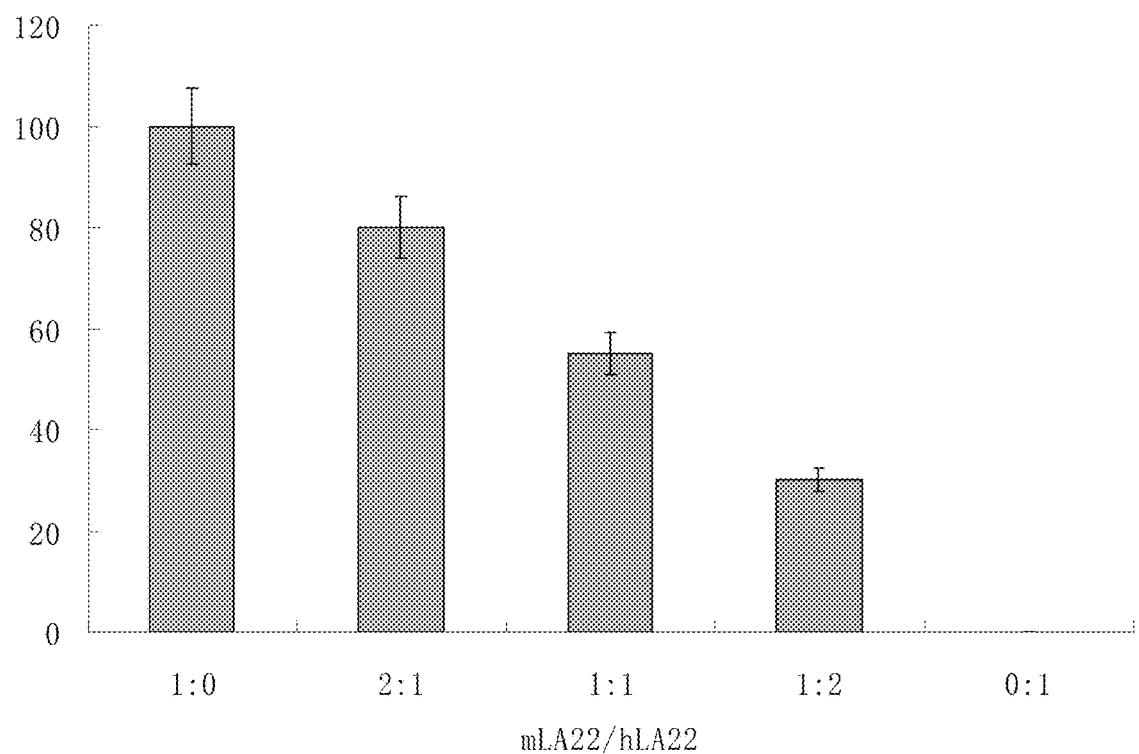
FIG. 14 Competition of binding to A431 cells between mLA22 and hLA22.

3. Cell ELISA assay A431 cells were seeded at 20,000 cells/well of 96-well plate in DMEM-10% FBS and incubated at 37° C. 5% $CO_2$. 24 hours later, discard the medium. After two washes with PBS and blocking with 5% skim-milk/PBS for 1 h, wells were incubated with different concentration of mLA22 and hLA22 in 5% skim-milk-PBS for another one hour. After two washes with PBS, wells were then incubated with HRP-conjugated goat anti-mouse IgG secondary antibodies or HRP-conjugated goat anti-human IgG secondary antibodies (Jackson Lab) in 5% skim-milk-PBS for 1 h at room temperature. After washes with PBS, HRP substrate 3, 3', 5, 5'-tetramethylbenzidine (TMB) solution was added. The reaction was stopped with stop solution (0.1M H2504) and absorbance was measured at 450 nm with a microplate reader. The results showed that mLA22 and hLA22 bind to the EGFR expressed on A431 cell surface and saturated at 4 µg/ml, indicating that the present invention of humanized antibody hLA22 h2H3 has the same affinity as mLA22 (FIG. 13).

4. Tumor cell proliferation inhibition test A431 cells were seeded at 20,000 cells/well of 96-well plate in DMEM-10% FBS and incubated at 37° C. 5% $CO_2$. 4 hours later, discard the medium and added 100 µl/well of different concentration of mLA22 and hLA22 in serum free DMEM at 37° C. 5% $CO_2$. Four days later, the cell numbers in each well were determined by MTT assay.

Tumor cell growth inhibition rate (%)=(DMEM containing no antibody treated cells number−antibody treated cells number)÷DMEM containing no antibody treated cells number×100%

Figure 15:
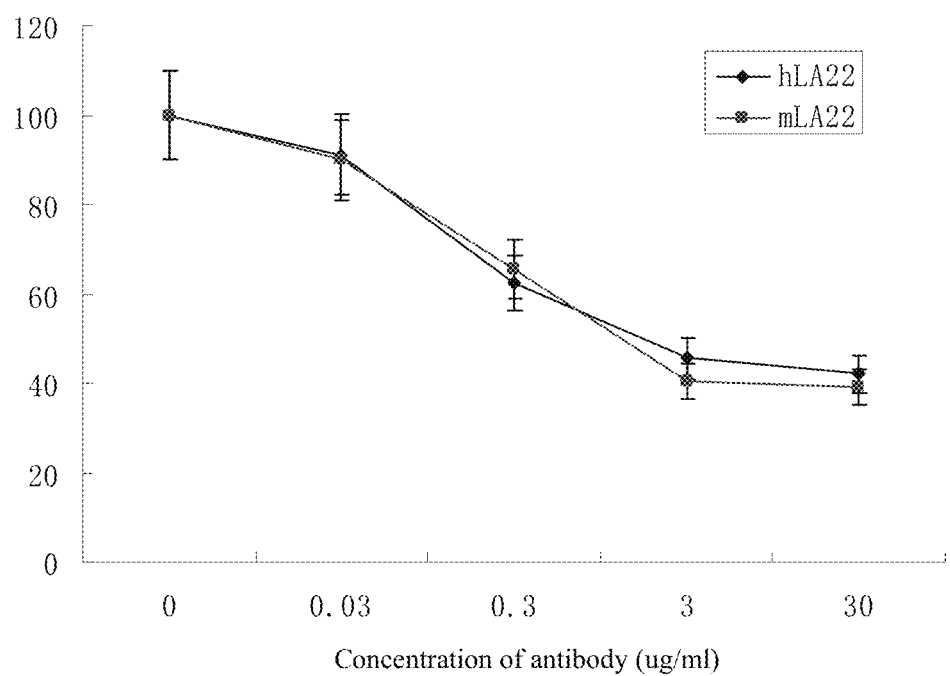
FIG. 15 Inhibition of tumor cell growth.

As shown in FIG. 15, mLA22 and hLA22 could inhibit the proliferation of A431 cells and humanized hLA22 remained the ability of mLA22 that inhibited tumor growth, both inhibitory effect were considerably.

INDUSTRIAL APPLICATIONS

The invention features humanized anti-EGFR antibodies which have 90% of the amino acid sequences from human, with affinity to EGFR in the range of 2.3 nM, which is very similar to the mouse anti-EGFR monoclonal antibody. Once bound to the surface EGFR, these new anti-EGFR antibodies internalize rather quickly, which made them ideal candidate for antibody drug conjugation and other biotherapy. Humanization will significantly reduce the risk of human anti-mouse immunogenicity, extend its half-life and increase the efficacy of the biological drugs.

---

What is claimed is:

1. A humanized anti-EGFR monoclonal antibody comprising any one of heavy chain amino acid sequences of SEQ ID NO. 1, or 7-11 and any one of light chain amino acid sequences of SEQ ID NO. 2 or 12-14, and the constant regions from human IgG1 kappa.

2. The humanized anti-EGFR monoclonal antibody of claim 1, wherein the humanized light chain amino acid sequence comprises SEQ ID NO. 2, and the humanized heavy chain amino acid comprises SEQ ID NO. 1.

3. The humanized anti-EGFR monoclonal antibody of claim 1, wherein the humanized light chain amino acid sequence comprises SEQ ID NO. 14.

4. The humanized anti-EGFR monoclonal antibody of claim 1, wherein the humanized heavy chain amino acid sequence comprises SEQ ID NO. 10.

5. The humanized anti-EGFR monoclonal antibody of claim 1, wherein the humanized light chain amino acid sequence comprises SEQ ID NO. 14 and the humanized heavy chain amino acid sequences of SEQ ID NO. 10.

6. A DNA sequence encoding an antibody of claim 1.

7. A DNA sequence of claim 6, wherein the humanized anti-EGFR monoclonal antibody comprises the humanized light chain gene sequence of SEQ ID NO. 22, and the humanized heavy chain gene sequence of SEQ ID NO. 18.

8. An expression plasmids containing the DNA sequence of claim 7.

9. A therapeutic composition comprising the antibody of claim 1.

10. A diagnostic kit comprising the antibody of claim 1.

11. A method for killing or inhibiting the growth of cancer cells, comprising contacting the cancer cells with an EGFR-binding molecule according to claim 1.

12. The method of claim 11, wherein the cancer cells are lung cancer cells.

13. The therapeutic composition of claim 9, wherein the antibody comprises the humanized light chain amino acid sequence of SEQ ID NO. 2, and the humanized heavy chain amino acid sequence of SEQ ID NO. 1.

14. The therapeutic composition of claim 9, wherein the antibody comprises the humanized light chain amino acid sequence of SEQ ID NO. 14.

15. The therapeutic composition of claim 9, wherein the antibody comprises the humanized heavy chain amino acid sequence of SEQ ID NO. 10.

16. The therapeutic composition of claim 9, wherein the antibody comprises the humanized light chain amino acid sequence of SEQ ID NO. 14 and the humanized heavy chain amino acid sequence of SEQ ID NO. 10.

17. The diagnostic kit of claim 10, wherein the antibody comprises the humanized light chain amino acid sequence of SEQ ID NO. 2, and the humanized heavy chain amino acid sequence of SEQ ID NO. 1.

18. The diagnostic kit of claim 10, wherein the antibody comprises the humanized light chain amino acid sequence of SEQ ID NO. 14.

19. The diagnostic kit of claim 10, wherein the antibody comprises the humanized heavy chain amino acid sequence of SEQ ID NO. 10.

20. The diagnostic kit of claim 10, wherein the antibody comprises the humanized light chain amino acid sequence of SEQ ID NO. 14 and the humanized heavy chain amino acid sequence of SEQ ID NO. 10.

* * * * *